United States Patent
Mauderli et al.

(10) Patent No.: US 6,644,244 B2
(45) Date of Patent: Nov. 11, 2003

(54) APPARATUS AND METHODS FOR TESTING PAIN SENSITIVITY

(75) Inventors: Andre Paul Mauderli, Dunnellon, FL (US); Charles J. Vierck, Gainesville, FL (US)

(73) Assignee: University of Florida, Gainesville, FL (US)

( * ) Notice: Subject to any disclaimer, the term of this patent is extended or adjusted under 35 U.S.C. 154(b) by 102 days.

(21) Appl. No.: 10/004,662

(22) Filed: Dec. 5, 2001

(65) Prior Publication Data

US 2003/0105412 A1 Jun. 5, 2003

(51) Int. Cl.[7] .............................................. A01K 29/00
(52) U.S. Cl. ...................................... 119/417; 119/421
(58) Field of Search ................................ 119/417, 418, 119/421, 712, 719, 720, 721

(56) References Cited

U.S. PATENT DOCUMENTS

| | | | | |
|---|---|---|---|---|
| 2,244,082 | A | * 6/1941 | Reyniers | 600/21 |
| 3,693,590 | A | * 9/1972 | Bowers | 119/421 |
| 4,337,726 | A | * 7/1982 | Czekajewski et al. | 119/421 |
| 4,574,734 | A | * 3/1986 | Mandalaywala et al. | 119/421 |
| 4,968,974 | A | * 11/1990 | Sakano | 340/573.3 |
| 5,608,209 | A | * 3/1997 | Matsuda | 250/221 |
| 5,721,207 | A | * 2/1998 | Noble et al. | 514/9 |
| 5,915,332 | A | * 6/1999 | Young et al. | 119/421 |
| 6,062,224 | A | * 5/2000 | Kissinger et al. | 128/897 |
| 6,223,690 | B1 | * 5/2001 | Park | 119/248 |
| 6,273,026 | B1 | * 8/2001 | Ferster et al. | 119/421 |
| 6,345,943 | B1 | * 2/2002 | Lawson et al. | 410/29.1 |
| 2003/0024482 | A1 | * 2/2003 | Gondhalekar et al. | 119/417 |

OTHER PUBLICATIONS

U.S. patent application Ser. No. 10/313,636, Mauderli et al., filed Dec. 5, 2002.

Bohus, B. and D. Wied "Avoidance and escape behavior following medial thalamic lesions in rats" *J Comp Physiol Psychol* [1967] 64(1):26–29.

Chaplan, S.R. et al. "Quantitative assessment of tactile allodynia in the rat paw" *J Neurosci Methods* [1994] 53:55–63.

Chapman, C.R et al. "Pain Measurement—an Overview" *Pain* [1985] 22:1–31.

Cleary, A. *Instrumentation for Psychology* [1977] pp. 131–222.

D'Amour, F.E. and D. Smith "A method for determining loss of pain sensation" *J Pharmacol Exp Ther* [1941] 72:74–79.

Dubner, R. "Methods of assessing pain in animals" *Textbook of Pain* [1989], pp. 247–256.

Dubuisson, D and S.G. Dennis "The formalin test: a quantitative study of the analgesic effects of morphine, meperidine, and brain stem stimulation in rats and cats" *Pain* [1977] 4:161–174.

Hargreaves, K et al. "A new and sensitive method for measuring thermal nociception in cutaneous hyperalgesia" *Pain* [1988] 32:77–88.

(List continued on next page.)

*Primary Examiner*—Yvonne Abbott
(74) *Attorney, Agent, or Firm*—Saliwanchik, Lloyd & Saliwanchik (57) ABSTRACT

The subject invention concerns an apparatus for testing pain sensitivity in an animal. The apparatus can be used to evaluate pain sensitivity in response to a disease state, drug, surgical procedure, or other intervention. The subject invention also pertains to methods for testing pain sensitivity in an animal, using the apparatus. The apparatus of the subject invention can be automated and used in conjunction with software for control of experimental conditions, response measurements, and data analysis.

39 Claims, 2 Drawing Sheets

OTHER PUBLICATIONS

Mauderli, A.P. et al. "An operant assay of thermal pain in conscious, unrestrained rats" *J Neurosci Methods* [2000] 97:19–29.

McGrath, P.A. et al. "Masseter inhibitory periods and sensations evoked by electrical tooth pulp stimulation" *Pain* [1981] 10:1–17.

Randall, P.K. and D.C. Riccio "Fear and punishment as determinants of passive–avoidance responding" *J Comp Physiol Psychol* [1969] 69(3):550–553.

Sandkuhler, J. and G.F. Gebhart "Characterization of inhibition of a spinal nociceptive reflex by stimulation medially and laterally in the midbrain and medulla in the pentobarbital–anesthetized rat" *Brain Res* [1984] 305:67–76.

Vierck, C.J. et al. "Behavioral analysis of CNS pathways and transmitter systems involved in conduction and inhibition of pain sensation and reactions in primates" *Progress in Psychobiology and Physiological Psychology* [1983] pp. 113–165.

Vierck, C.J. and B.Y. Cooper, "Guidelines for assessing pain reactions and pain modulation in laboratory animal subjects" *Advances in Pain Research and Therapy* [1984], pp. 305–322.

Vierck, C.J. et al. "Inference of pain sensitivity from complex behaviors of laboratory animals" *Issues in Pain Measurement* [1989] pp. 93–115.

Willer, J.C. et al. "Supraspinal influences on nociceptive flexion and pain sensation in man" *Brain Res* [1979] 179:61–68.

Woolfe, G and A.D. MacDonald, "The evaluation of the analgesic action of pethidine hydrochloride (Demerol)" *J Pharmacol Exp Ther* [1944] 80:300–307.

* cited by examiner

APPARATUS AND METHODS FOR TESTING PAIN SENSITIVITY

The subject invention was made with government support under a research project supported by National Institutes of Health Grant Nos. RO1 NS07261, T32 DE07200, and K15 DE00375. The government has certain rights in this invention.

BACKGROUND OF THE INVENTION

Pain is an experience that cannot be measured directly, either in humans, or in animals, but must be inferred from behaviors. The available repertoire of behaviors that consistently reveal pain includes verbalizations in humans and complex motor sequences that eliminate nociceptive stimulation (escape responses) in humans and other animals. A variety of other behaviors suggest the presence of pain but can be elicited by stimuli or situations that are not necessarily aversive or involve responses that do not require a conscious perception of pain. Pain tests for non-human animals have been reviewed extensively in the literature (Vierck, C. J., B. Y. Cooper, *Advances in Pain Research and Therapy* [1984], pp. 305–322; Chapman, C. R et al., *Pain* [1985] 22:1–31; Dubner, R. *Textbook of Pain* [1989], pp. 247–256; Franklin, K. B. J and F. V. Abbott, *Neuronmethods, Psychopharmacology* [1989] 13:145–215; Vierck, C. J. et al. *Issues in Pain Measurement* [1989] pp. 93–115), and they can be classified according to two main criteria: (1) type of stimulus applied; and (2) type of response measured.

Some methods for evaluating phasic responses to nociceptive stimulation involve electrical stimulation, because it can be turned on and off instantly, making it easy for an animal to learn the temporal relationship between an escape response and elimination of an aversive sensation. Although electrical stimulation has been criticized because skin receptors are bypassed, and synchronous afferent firing patterns are generated (Dubner, R., 1989), it is possible to elicit natural sensations of predictable quality when electrode tissue coupling is tightly controlled (Vierck, C. J. et al., *Animal Pain Perception and Alleviation: American Physiological Society* [1983] pp. 117–132; Vierck, C. J. et al., 1989; Vierck, C. J. et al., *Somatosens Mot Res* [1995] 12:163–174). However, control over current density and stimulus location can be achieved only by restraining the subjects, and animals will tolerate restraint only after lengthy adaptation and training periods. Restraint without proper adaptation leads to high levels of stress and anxiety—factors that are known to have modulatory effects on pain sensitivity (Amir, S. and Z. Amit, *Life Sci* [1978] 23:1143–1151; Bhattacharya, S. K. et al., *Eur J Pharmacol* [1978] 50:83–85; Basbaum, A. I. and H. L. Fields, *Annu Rev Neurosci* [1984] 7:309–338; Franklin, K. B. J. and F. V. Abbott, 1989; Maier, S. F. et al., *APS J* [1992] 1:191–198; Tokuyama, S. et al., *Jpn J Pharmacol* [1993] 61:237–242; Caceres, C. and J. W. Burns, *Pain* [1997] 69:237–244). Therefore, nociceptive tests that require restraint or extensive handling, which have an effect on pain processing, may produce contaminated results.

Thermal stimulation has been used previously for nociceptive tests (Dubner, R., 1989). Contact thermal stimulation provides the basis for the hotplate test (Woolfe, G and A. D. Macdonald, *J Pharmacol Exp Ther* [1944] 80:300–307), and extensive use of contact heat in psychophysical and neurophysiological studies has established the range of temperatures that produces heat nociception. Radiant heat is used in the tailflick test (D'Amour, F. E. and D. Smith, *J Pharmacol Exp Ther.* [1941] 72:74–79) and the Hargreaves hindlimb-withdrawal test (Hargreaves, K et al., *Pain* [1988] 32:77–88). The absence of a concurrent mechanical stimulus is thought to be an advantage of radiant heat, but it is difficult to control and assess skin temperature. Observations of hindlimb withdrawal and/or guarding behavior have also been utilized to evaluate thresholds for reactivity to mechanical stimulation (Chaplan, S. R. et al. *J Neurosci Methods* [1994] 53:55–63) or the frequency of responsivity to chemical stimulation (Dubuisson, D and S. G. Dennis, *Pain* [1977] 4:161–174). A present difficulty with mechanical tests is that characteristics of von Frey filaments (e.g. combinations of diameter and force) which produce mechanical nociception have not been determined. Chemical stimuli can be varied in concentration, volume and method of application (injection or surface application), but it is difficult to characterize the effects of these agents on peripheral tissues, receptors and afferents. These different methods of nociceptive testing elicit responses that can be modulated differentially by a variety of treatments (Willer, J. C. et al. *Brain Res* [1979] 179:61–68; McGrath, P. A. et al., *Pain* [1981] 10:1–17; Vierck, C. J. et al., *Progress in Psychobiology and Physiological Psychology* [1983b] pp. 113–165; Sandkuhler, J. and G. F. Gebhart, *Brain Res* [1984] 305:67–76; Dubner, R., 1989), and it is often concluded that the method of stimulation is the determinant factor, without consideration of other aspects of the testing method and response measurement.

An important consideration in evaluation of nociceptive tests is the central circuitry that is interposed between the input and output stages. For example, the tail flick and paw withdrawal responses can be elicited in spinal animals (Franklin, K. B. J. and F. V. Abbott, 1989) and therefore can represent segmental spinal reflexes. Pawlicking in the hotplate test (Woolfe, G. and A. D. Macdonald, 1944; Eddy, N. B. et al., *J Pharmacol Exp Ther* [1950] 98:121–137; Chapman, C. R et al., 1985) and vocalization (Carroll, M. N and R. K. S. Lim, *Arch Int Pharmacodyn* [1960] 125:383–403) can be elicited in chronic decerebrate rats (Woolf, C. J., *Pain* [1984] 18:325–343; Berridge, K. C., *Behav Brain Res* [1989] 33:241–253; Matthies, B. K. and K. B. Franklin, *Pain* [1992] 51:199–206) and can be modulated differentially from responses to the same stimulus that originate at higher levels of the neuraxis (Sandkuhler, J. and G. F. Gebhart, 1984; Cooper, B. Y. and C. J. Vierck, *Pain* [1986] 26:393–407; Dubner, R., 1989). Therefore, it is important to distinguish innate responses that can be segmental (spinal) reflexes or long-loop (spino-bulbospinal) reflexes from operant responses that necessarily employ complex learned motor actions (involving the cerebrum).

Animal models of pain are most useful when they are good predictors of the effect of disease states or therapeutic interventions on human clinical pain. The clinically most relevant consequence of nociceptive stimuli is the conscious experience of pain and suffering that the stimuli may elicit. Assays based upon short or long-loop reflexes (such as the tail-flick test, paw withdrawal test, or hotplate test) provide little or no insight into what goes on at the conscious level. Reflex tests and the few available assays of conscious responses to painful stimuli, such as the foot shock escape test, rely mostly on fast-conducting pain pathways. However, it is known that slow-conducting nociceptive systems are the major contributors to the conscious experience of clinical pain and they are primarily affected by powerful pain killers such as morphine.

Shuttle-box paradigms, using the operant response measure of learned escape have been popular models of conscious aspects of pain (Warner, L. H., *J Genetic Psychol* [1932] 41:57–89; Bohus, B. and D. Wied, *J Comp Physiol Psychol* [1967] 64:26–29; Randall, P. K. and D. C. Riccio, *J Comp Physiol Psychol* [1969] 69:550–553; Cleary, A. *Instrumentation for Psychology* [1977] pp. 1–319). These methods are easy to implement, because the subjects are unrestrained. Electrical stimulation has been used in shuttle box paradigms because it can be regulated in intensity and switched between chambers. However, it is problematic in these situations, because movement of the animals across a grid floor switches polarities and varies current densities.

A shuttle-box test was developed which uses thermal nociceptive stimulation (hot or cold), as opposed to electrical stimulation (Mauderli, A. P. et al., *J Neurosci Methods* [2000] 97:19–29). The thermal stimulus is transmitted from a thermal plate on the floor of a compartment to the paws of the freely moving animals. However, through training, the animals learn that they can escape the stimulus by moving from the heated compartment, which is kept dark, onto a non-heated platform within an enclosure, which is suspended within the heated compartment. Thus, the enclosed platform represents the destination for escape from the thermal plate. However, to discourage avoidance behavior, the escape platform is made less attractive by brightly illuminating it and imposing a degree of tilt toward the dark compartment. The thermal plate is kept constantly heated by internal water circulation and a new trial is started by swinging the enclosure into a vertical position, thereby ejecting the animal onto the thermal plate.

Tests of nociception are most often used to evaluate pharmacological, disease, or surgical effects on pain. However, these effectors may alter the measured behaviors through mechanisms other than pain. Morphine, for instance, may make the animal sluggish in response to any stimulus, including non-painful stimuli. Therefore, it is necessary to pair any pain test with a valid control test for non-pain-related effects, such as attentional, motivational and motor effects (Dubner, R., 1989). To be valid, treatment effects on escape should be compared with effects on a control task that involves a comparable motivation (escape) and the same motor response (e.g. stepping on a platform) as the nociceptive test. The rotarod test (Dunham, N. W. and T. S. Miya, *J Am Pharm Assoc* [1957] 46:208–209; Kinnard Jr., W. J. and C. J. Carr, *J Pharmacol Exp Ther* [1957] 121:354–361) for instance, cannot be considered an adequate control for a reflex-based test or an operant shuttle-box assay of nociception, because the motor tasks and motivations differ considerably for these tests.

A control test for the thermal escape test was developed (Mauderli, A. P. et al., 2000), which measures latencies for escape from a bright light (controlling for generalized effects on aversion). In this arrangement, a two-chambered box that uses only bright light as the behavioral driving force is utilized for motor and general motivational effects for the thermal pain test, which is conducted in a separate apparatus. Therefore, the motor task in the control test is similar to that required by the thermal escape test, in that both involve escape into another compartment and use of a bright light. However, there are differences in the apparatuses used in the control test and thermal escape test that may limit their effectiveness. The differences in design between the two apparatuses requires that each animal be trained on both tasks and be able to distinguish between them. In addition, responses in the thermal escape test are always directed toward the same compartment (a one-way shuttle test), but the control test is a two-way test, because the aversive light can occur in either of the two chambers. A one-way shuttle test carries the risk that the animal can learn to associate between "comfort" and a specific compartment or location. . In addition, for experimental treatments that influence memory, it can be a drawback if the difficulty level of the two tests is not the same.

It is evident that the behavioral testing devices currently available may be of limited use as research tools with respect to nociception. Accordingly, there remains a need for a device which is capable of testing pain based upon a conscious response, permits assessment of slowly-conducting pain systems, avoids restraint stress, minimizes animal handling artifacts, and is matched with a valid behavioral and motor control test.

THE BRIEF SUMMARY OF THE INVENTION

The subject invention concerns an apparatus for testing pain sensitivity exhibited by an animal. The apparatus can be used, for example, to evaluate the effect of a disease state, drug, or other intervention, on pain sensitivity. The apparatus is designed to measure a conscious escape response to a painful stimulus in test animals, such as rodents. The apparatus of the subject invention provides an inclusive operant pain test and a matching motor control test. The subject invention also pertains to methods for testing the pain sensitivity exhibited by a test animal, using the subject apparatus.

The apparatus of the subject invention includes two chambers, a first chamber and a second chamber, which are connected by a passageway. The passageway is of sufficient size to permit the test animal to pass between the chambers. Preferably, the passageway is designed such that the test animal can pass through the passageway even if the test animal is tethered to infusion cannula(s), cable(s), or other diagnostic and/or delivery device(s). The apparatus also includes means for producing a painful condition in the first chamber and a means for producing a painful condition in the second chamber. Each means for producing a painful condition can be independently activated and deactivated within each of the chambers. Each painful condition can be independently and rapidly produced and independently and rapidly removed within the respective chamber. The apparatus further includes means for producing an aversive, non-painful condition in the first chamber and a means for producing an aversive, non-painful condition in the second chamber. The means for producing an aversive, non-painful condition in the first and second chamber can each motivate the test animal to exit the chamber in which the aversive, non-painful condition is produced. The means for producing an aversive, non-painful condition can be independently activated and deactivated within each of the chambers. Each aversive, non-painful condition can be independently and rapidly produced and independently and rapidly removed from the respective chamber. Each means for producing a painful condition creates a condition that is painful to the test animal within the chamber where the means for producing the painful condition is activated and in which the painful condition is produced. The means for producing a painful condition in the first and second chamber each create a condition that is aversive to the test animal such that the test animal can be motivated to exit the chamber in which the painful condition is produced. Therefore, the net effect of producing a painful condition and/or an aversive, non-painful condition within the chamber that the test animal is present in, is that the test animal can be motivated to exit the chamber it is occupying and move through the passageway into another chamber.

Preferably, each means for producing an aversive, non-painful condition is one or more light sources for lighting the interior of the respective chamber. Preferably, each means for producing a painful condition is a means for independently heating and cooling the respective chamber floor.

The apparatus can also include means for sensing the presence of the test animal within the first chamber and a means for sensing the presence of the test animal within the second chamber. The apparatus can be automated and used in conjunction with computer software for control of experiment conditions, response measurements, and data analysis.

The subject invention also concerns methods for using the subject apparatus to conduct escape latency tests, place preference tests, and control tests for each.

DETAILED DISCLOSURE OF THE INVENTION

The subject invention concerns an apparatus 10 for testing the pain sensitivity exhibited by a test animal 30. The apparatus 10 can be used to evaluate the pain sensitivity of the test animal 30 in response to a disease state, drug, or other intervention, such as a surgical procedure. The apparatus 10 is designed to measure a conscious escape response to a painful stimulus in a test animal 30. The subject invention also pertains to methods for evaluating pain sensitivity exhibited by a test animal 30, in response to a drug, disease condition, or other intervention, using the subject apparatus 10.

The apparatus 10 of the subject invention includes two chambers, a first chamber 12 and a second chamber 14, connected by a passageway 16. The passageway 16 is of sufficient size to permit the test animal 30 to pass between the chambers 12, 14. The apparatus 10 also includes means for producing a painful condition within said first chamber 12 and means for producing a painful condition within said second chamber 14. Each painful condition can be independently and rapidly produced in the respective chamber and independently and rapidly removed from the respective chamber. The apparatus 10 further includes means for producing an aversive, non-painful condition within each of the chambers 12, 14. Each aversive, non-painful condition can be independently and rapidly produced in the respective chamber and independently and rapidly removed from the respective chamber. The apparatus 10 can also include means for sensing the location of the test animal 30 within the apparatus 10 (e.g., which chamber the test animal 30 is in). Each means for producing an aversive, non-painful condition creates a condition that is aversive to the test animal 30 within each chamber 12, 14 where the means for producing an aversive, non-painful condition are activated. Preferably, each means for producing a painful condition and each means for producing an aversive, non-painful condition is adjustable in its intensity.

As used herein, the term "rapidly produced" means that an aversive environment or condition is rapidly created within the particular chamber 12, 14 that the means for producing the painful condition and/or the means for producing the aversive, non-painful condition are activated. The term "rapidly removed" means that an aversive environment or condition is rapidly removed from within the particular chamber 12, 14 that the means for producing the painful condition and/or the means for producing the aversive, non-painful condition are de-activated. Preferably, a painful condition and an aversive, non-painful condition can each be produced in each chamber in about 30 seconds or less, and a painful condition and an aversive, non-painful condition can each be removed from each chamber in about 30 seconds or less. More preferably, a painful condition and an aversive, non-painful condition can each be produced in each chamber in about 10 seconds or less, and a painful condition and an aversive, non-painful condition can each be removed from each chamber in about 10 seconds or less. Most preferably, a painful condition and an aversive, non-painful condition can each be produced in each chamber in about 5 seconds or less, and a painful condition and an aversive, non-painful condition can each be removed from each chamber in about 5 seconds or less.

Each chamber 12, 14 has a surface for supporting the test animal 30 (e.g., a floor). Each floor 18, 20 can be a continuous surface or a perforated surface (e.g., a wire mesh). The chamber floors 18, 20 should be of sufficient surface area to enable the particular type of test animal 30 being used to move about the apparatus 10. For example, where the test animal 30 is a rat, the first and second chambers 12, 14 can each be about 22 cm×22 cm×24 cm.

Preferably, the means for producing a painful condition in the first chamber 12 is a means for independently heating and cooling 22 the first chamber floor 18, and the means for producing a painful condition in the second chamber 14 is a means for independently heating and cooling the second chamber floor 20, such that thermal pain stimulation (e.g., aversive heat or aversive cold) can be provided to the paws of the test animal 30 while they contact either of the chamber floors 18, 20. When the means for producing the painful condition are means for independently heating and cooling the chamber floors 18, 20, each of the chamber floors 18, 20 are preferably composed of a thermally conductive material that is corrosive resistant, such as copper or aluminum. More preferably, the chamber floors 18, 20 are composed of copper.

More preferably, one or more thermoelectric modules ("TEMs"; also known as Peltier devices) 24 located beneath each of the chamber floors 12, 14, can be used as heat pumps to move heat to and from the chamber floors 12, 14. A TEM 24 contains a number of p-type and n-type pairs (couples) connected electrically in series and sandwiched between two ceramic plates. When connected to a DC power source, current causes heat to move from one side of each TEM 24 to the other side, creating a hot side and a cold side. If the current is reversed (reversing the polarity of the power supply), the heat is moved in the opposite direction, with the hot face becoming the cold face and vice-versa. TEMs 24 are particularly well suited for use in the apparatus 10 of the subject invention because they are solid-state devices that can provide precision temperatures, with no moving parts. Therefore, they produce virtually no noise to distract the test animal 30, which could potentially skew experimental results. The amount of heat pumped through the TEM 24 is directly proportional to the power supplied. Temperature can be controlled through manual or automatic means. The automatic temperature controller utilized can range in complexity from a simple on-off thermostat to a complex computer controlled feedback proportional control loop.

The TEMs 24 are located beneath, and preferably in contact with, the chamber floors 18, 20. More preferably, the TEMs 24 are located between the chamber floors 18, 20 and a heat sink 26. There are at least two heat sinks, one heat sink 26 beneath, and in contact with, each chamber floor. Each heat sink 26 is preferably a liquid-type heat sink composed of aluminum and containing channels 28 to remove heat from the surface of the TEM 24 that contacts it, or to supply heat to the surface of the TEM 24 that contacts it, depending upon the direction the heat is pumped by the TEM 24. Other types of heat sinks, such as fin-type heat sinks, with or without fans, can also be utilized.

In order to maximize heat transfer between each TEM 24 and each heat sink 26, and between each TEM 24 and the corresponding chamber floor, a film of heat conducting medium, such as zinc oxide paste, can be applied to the top and bottom surface of the TEM 24.

By using one or more TEMs 24 as the heating and cooling means 22 beneath each chamber floor 18, 20, it is possible to modulate the temperature of the chamber floors 18, 20 very rapidly from an aversive temperature to a neutral, steady-state temperature (e.g., 39° C.), and vice-versa, and ranges there between. For example, it is possible to modulate the temperature of the chamber floors 18, 20 about 10° C. in about ten seconds or less, and even five seconds or less, within a temperature range of about 0° C. to about 60° C.

When using means for independently heating and cooling the chamber floor, aversive cold temperatures can be from about 0° C. to about 10° C. for cold stimulus or about 43° C. to about 49° C. for heat stimulus. Preferably, temperatures from about 0° C. to about 1° C. are used for cold stimulus, temperatures from about 43° C. to about 45° C. are used for heat stimulus to test slow conducting nerve fiber systems, and temperatures from about 47° C. to about 49° C. are used for heat stimulus to test fast conducting nerve fiber systems.

Another means for producing a painful condition within each chamber, that can be independently and rapidly produced and removed, involves placement of one heat sink 26 beneath, and in contact with, each chamber floor. However, instead of utilizing one or more TEMs 24 beneath each chamber floor, each heat sink 26 is connected with a source of hot liquid and a source of cold liquid, with flow between the heat sink 26 and the sources of hot and cold liquid controlled by one or more valves. The hot and cold liquid can be rapidly pumped into and out of the heat sink 26, as required, by one or more liquid pumps. In another embodiment, instead of being located beneath the chamber floor, each heat sink 26 can itself serve as the chamber floor.

Both means for producing a painful condition can be a single "unit" that can be manipulated (manually or automatically) to administer a pain stimulus to the test animal within either chamber, such as an array of TEMs that are moved from beneath one chamber floor to another chamber floor, as required. Preferably, the means for producing the painful condition represents two separate units, such as an array of TEMs located beneath each chamber floor. Although separate, each unit can be in operable communication.

The passageway 16 is of sufficient size for the test animal 30 to pass freely between the chambers 12, 14. For example, where the test animal 30 is a rat, the passageway 16 can be about 6.5 centimeters wide. Preferably, the passageway 16 has no overhead door jam, thereby permitting unfettered passage of the test animal 30 if the animal is tethered, e.g., with electrical leads, microdialysis tubes, or other diagnostic or drug delivery devices. It is also preferred that the passageway 16 be sufficiently short (such as a portal), such that the test animal 30 will always be in contact with at least one of the chamber floors, thereby requiring the test animal 30 to pass from one chamber directly to another.

The apparatus 10 of the invention includes means for producing an aversive, non-painful condition within the first chamber 12 and means for producing an aversive, non-painful condition within the second chamber 14. Each means for producing an aversive, non-painful condition creates an aversive condition within the particular chamber that the means for producing the aversive, non-painful condition is activated.

Figure 1:
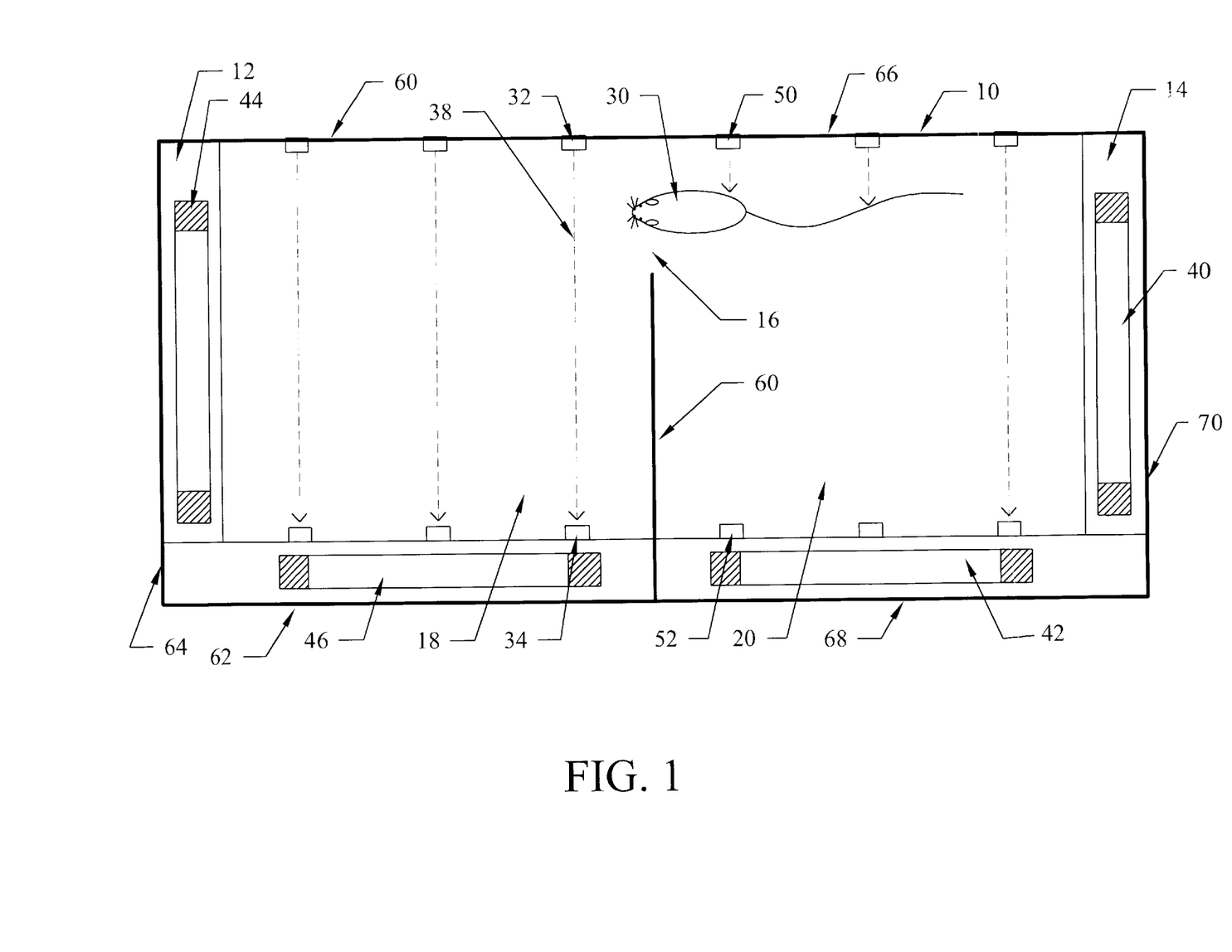
FIG. 1 shows an overhead view of one embodiment of the apparatus of the subject invention.

Preferably, each means for producing an aversive, non-painful condition is one or more light sources for lighting the interior of the chambers 18, 20, such as a fluorescent light. If each means for producing an aversive, non-painful condition is one or more light sources, it is preferred that the passageway 16 be large enough to allow the test animal 30 to pass freely but sufficiently small to minimize the amount of light that enters each chamber 12, 14 when one chamber is dark and the other chamber is lit. In a specific embodiment, the first chamber 12 has two light sources 40 and 42, and the second chamber 14 has two light sources 44, 46, as shown in FIG. 1.

Other means for producing an aversive, non-painful condition, which can be independently and rapidly produced and removed, include means for producing a sound that is aversive to the test animal 30 (e.g., an electronic audio player), or means for producing a smell that is aversive to the test animal 30, for example. The aversive smell can be rapidly produced and removed by a fan or other circulation means.

The means for producing the aversive, non-painful condition can be a single "unit", such as a moveable light source that can be manipulated (manually or automatically) to direct aversive light into each chamber, or the means for producing the aversive, non-painful condition can be two separate units, such as separate light sources mounted within or adjacent to each chamber. Although separate, each unit can be in operable communication.

The location of the test animal 30 within the apparatus at a given time can be determined visually by an operator either directly or indirectly, e.g. with a video camera. However, the apparatus 10 of the subject invention can also include means for sensing the presence of the test animal 30 within each chamber 12, 14. Preferably, there is a means for sensing the presence of the test animal within the first chamber 12 and a means for sensing the presence of the test animal within the second chamber 14. More preferably, means for sensing the presence of the test animal in the first chamber includes one or more infrared beam emitters 32 and detectors 34 within the first chamber 12, where the beam emitters 32 and detectors 34 are operably positioned, producing one or more infrared beams 38 in the first chamber 12. Means for sensing the presence of the test animal in the second chamber 14 includes one or more infrared beam emitters 50 and detectors 52 in the second chamber 14, where the emitters 50, and detectors 52 are operably positioned, producing one or more infrared beams 38 in the second chamber 14. As used herein, the term "operably positioned" means that the emitters 32, 50 and detectors 34, 52 are at a predetermined position with respect to each other such that one or more infrared beams 38 are emitted and detected in each chamber, and interruption of the infrared beams 38 by the test animal 30 produces a signal indicating the location of the test animal 30 within the test apparatus 10 (e.g., indicating which chamber 12, 14 the test animal 30 is in). The apparatus 10 can also include means for measuring the relative amount of time the test animal 30 is present in each chamber 12, 14 and, optionally, determining the number of entries in each chamber 12,14.

In a separate embodiment, the apparatus 10 can include one or more infrared beam emitters and detectors within the passageway 16. Interruption of one or more infrared beams 38 produces a signal indicating that the test animal 30 has passed through the passageway 16. If the original position of the test animal 30 is known, the position of the test animal 30 within the apparatus (i.e., within which chamber) at a given time can be surmised based on the number of times the test animal 30 has passed back and forth through the passageway 16.

Other means for sensing the location of the test animal 30 within the apparatus 10 include ultrasound localization, digital image analysis, or monitoring electrical capacitance of the chamber floors 18, 20, for example.

In a preferred embodiment, the shape and dimensions of the chambers 12, 14 are substantially identical to one another. For purposes of the subject invention, in this context, the term "substantially identical" means that the particular test animal 30 used cannot discriminate between the two chambers 12, 14, based upon their shape and dimensions. It is preferred that the chambers 12, 14 be designed to provide non-distinct visual and tactile environments to minimize contextual differences.

The test animal 30 can be any animal having nociceptors (receptors for pain stimuli) and which is capable of exhibiting an escape response to a pain stimulus. Preferred animals are those having a physiology sufficiently similar to humans such that they provide relevant correlative data, as an animal model, for the particular treatment being conducted on the animal. Examples of appropriate animals include those of the order rodentia, such as members of the family muridae (e.g., mice, rats, hamsters, voles, lemmings, and gerbils), lagomorpha (e.g., rabbits, pikas, and hares), and caviidae (e.g., guinea pigs), or those of the order insectivora, such as members of the family soricidae (shrews) and talpidae (moles), and so forth. In addition, if a light source is used as the means for producing the aversive, non-painful condition, it is preferred that the test animal be one that has an aversion to brightly lit areas, such as rodents (Ogren, S. O., *Acta Physiol Scand Suppl*, [1985], 544:1–71).

The following experiments are described where the test animal 30 is a rat, each means for producing an aversive, non-painful condition is a light source, and each means for producing a painful condition is means for independently heating and cooling the floors of each chamber 22; however, it should be understood that other embodiments may be used. In most experiments, one chamber is kept thermally neutral and brightly lit. When introduced into the apparatus, the rat will move back and forth between chambers, but spend more time in the less aversive chamber. During each trial, the rat's place preference (relative amount of time spent in either chamber) can be determined and recorded. The direction of the aversiveness gradient (which chamber is hot and which chamber is light) can be randomly chosen, and changed periodically throughout the experiment, so the rat cannot learn to associate the aversive stimulus (hot floor) with any particular chamber. In other words, because the two chambers are, preferably, identical and the gradient of the two aversive forces (e.g., thermal and light) can be reversed within seconds, avoidance learning is prevented.

The capability of each aversive, non-painful condition and each painful condition to be independently and rapidly produced and independently and rapidly removed within each chamber (also referred to herein as "the reversible feature") prevents the test animal 30 from recognizing one of the chambers 12, 14 as potentially aversive. If the animal were to recognize a chamber as potentially aversive, it would lead to behavior based upon past experience (avoidance), rather than behavior triggered by pain perceived at the moment (escape). Therefore, this apparatus 10 measures a conscious escape response, which requires a higher level of neural processing than simple reflex behaviors. Conventional pain tests typically infer pain from spinal reflex responses, such as paw withdrawal and tail flick. Reflex tests are not well suited for measuring delayed pain from a low intensity thermal stimulus, but the delayed pain from such stimuli is a better model of persistent clinical pain than the sharp pain that is best for triggering reflexes. Therefore, the apparatus 10 permits evaluation of the effects of disease states, drugs, surgical procedures, or other interventions, on the delayed pain mediated by unmyelinated pain fibers, which is a better model of persistent clinical pain than tests measuring the early sharp pain that results from high stimulus intensities.

The apparatus 10 of the subject invention can be used to perform a variety of tests. An escape test can be conducted where the means for producing a painful condition is not activated in either chamber 12, 14 and the test animal 30 is introduced into the apparatus 10. An adaptation period may be granted. If means for independently heating and cooling the chamber floors is utilized as means for producing a painful condition, the test animal's paws can assume the neutral temperature of the chamber floors 12, 14 during this period. The first trial is started by activating the means for producing a painful condition in the occupied chamber, to the desired intensity of the test. If the test animal 30 perceives that particular intensity of the painful condition as aversive, the test animal 30 will escape into the other chamber. The delay in the escape into the other chamber serves as the response variable or response time (escape latency). This delay for the initial crossover event can be measured (e.g., by an observer or automatically, through means of sensing the presence of the test animal 30 within each chamber). After each trial, a timeout period can be granted where the means for producing a painful condition is not activated in either chamber. A new trial is initiated by activating the means for producing a painful condition in the chamber occupied by the test animal. The escape latency can then be measured again.

In order to determine the contribution of changes in general motivational state and motor factors to the observed latency changes, the escape test can be repeated, as a control test, where the means for producing an aversive, non-painful condition (e.g., bright light) are used, without either means for producing a painful condition being used. The escape latency from the chamber in which the aversive, non-painful condition is activated serves as the response variable for the control test (e.g., control escape latency).

A number of avoidance-suppressing features can be implemented, as well. In a typical protocol, the means for producing a painful condition is not always activated in the same chamber. Therefore, the test animal 30 cannot use location cues as predictors of a painful experience. Sporadically, trials can be conducted with the means for producing a painful condition deactivated in both chambers (e.g., both chambers are set to a neutral temperature). Consistent short-latency responses during these trials are indicative of avoidance learning. Frequent exposure to this type of catch trial helps to minimize the test animal's avoidance tendency (extinction effect). High incidence of avoidance during catch trials serves as a warning indicator of avoidance tendencies and thus the validity of results should be questioned. Additionally, trials can be conducted with the means for producing a painful condition activated in both chambers 12, 14, with the means for producing a painful condition set at a higher intensity in the chamber that the test animal 30 is escaping to (the escape chamber), than that chamber it is escaping from. An avoidance response will thus be penalized by exposure to a painful stimulus (extinction effect). The means for producing an aversive, non-painful condition can be activated in the escape chamber, while the other chamber has only the means for producing a painful condition activated. The aversive, non-painful condition (e.g., light) discourages avoidance. However, escape will occur when the behavior driving force from the painful condition (e.g., heat or cold) overcomes the opposing driving force from the aversive, non-painful condition (e.g., light).

A place preference test is preferably conducted, which differs from the escape test by measuring the relative amount of time spent in the two chambers 12, 14 during each trial instead of the latency of the first crossing event between chambers. Higher pain sensitivity is inferred when the place preference is biased toward the chamber or chambers where the means for producing a painful condition is not activated (e g., the thermally neutral chamber) and, optionally, the means for producing an aversive, non-painful condition is activated. Conversely, the test animal 10 is inferred to have lower pain sensitivity when it is willing to spend more time (and does spend more time) in the chamber or chambers where the means for producing a painful condition is activated (e.g., the chamber or chambers with the hot floor). A shift in place preference (this test's response time) can be used to infer a change in pain sensitivity, e.g., due to drug effects and/or disease state. In most experiments, the means for producing the aversive, non-painful condition will be activated in the chamber where the means for producing the painful condition is not activated (e.g., the thermally neutral chamber will be brightly lit). However, this is not a requirement.

A test of general motivation and motor ability can be conducted with the place-preference test, as well, where the means for producing a painful condition are not activated in the chambers (e.g., the floors of the chambers are a neutral, non-aversive temperature) and only the means for producing an aversive, non-painful condition (e.g., light) are used as an aversive force. A pain-relieving effect of a drug or other intervention can be inferred when the place preference (the environment the animal spends relatively more time in) in the pain sensitivity test shifts toward the chamber or chambers where the means for producing a painful condition was activated (e.g., the hot chamber), but remains unchanged when only the means for producing an aversive, non-painful condition (e.g., light) are used as the aversive force (the control test). The apparatus of the subject invention is particularly suited to perform these tests because it uses a conscious response to infer pain (not a reflex). This is important because withdrawal reflexes and conscious perception of pain do not always go hand in hand. The control test for motor deficits or general motivational depression uses the same motor task as the test using the painful stimulus and thus is a well-matched and valid control.

Generally, the test animal 30 is trained to escape thermal stimulation by first acclimating it to the apparatus, with the chamber floors at a neutral temperature (e.g., 39° C.). A few trials at about 45° C. will allow the animal to learn the position of the passageway 16 relative to the chambers 12, 14.

Each trial of most testing sessions will begin with the introduction of the animal into the apparatus. The test animal 30 can be introduced into the apparatus 10 by placing the test animal 30 in one of the chambers or, for example, by permitting the test animal 30 to enter one of the chambers through a door (e.g., guillotine door) that can be built into one or both of the chambers 12, 14. The means for producing an aversive, non-painful condition can be activated in both chambers before or after the test animal 30 is introduced into the apparatus 10. The choice of the trial duration depends on the needs of an experiment and, where the means for producing a painful condition are means for independently heating and cooling the floors of the chambers, the temperature of the floor can also be a determinant. Experiments using short acting drugs can require brief trial durations. However, continuous drug infusion can be conducted by means of continuous drug delivery devices, such as a flexible cannula, to which the test animal 30 can be tethered. After each trial, a timeout period can be granted (e.g., about 2 to about 4 minutes) where the means for producing a painful condition in the chambers are not activated. Subsequently, a new trial can be initiated by activating the means for producing a painful condition to a nociceptive level, in the chamber occupied by the test animal. A trial period can be about 8 minutes to about 12 minutes, particularly where means for independently heating and cooling the chamber floors are used and lower temperatures (about 43° C. to about 45° C.) are utilized. Where higher temperatures (about 47° C. to about 49° C.), a shorter trial period from about 1 minute to about 3 minutes is preferred.

The apparatus 10 of the subject invention can be partially or fully automated. Therefore, the apparatus can also include means for automating the means for producing a painful condition and the means for producing an aversive, non-painful condition in response to the sensing means in both chambers. The automation means can be in operable communication with the features being automated. For example, when the test animal 30 passes through the passageway 16 from the first chamber 12 to the second chamber 14, the means for producing an aversive, non-painful condition in the second chamber 14 can be automatically activated or deactivated, and when the test animal 30 passes through the passageway 16 from the second chamber 14 to the first chamber 12, the means for producing an aversive, non-painful condition in the first chamber 12 can be automatically activated or deactivated. The same automation can be achieved with the means for producing a painful condition in the first chamber and the means for producing a painful condition in the second chamber.

Because the apparatus 10 of the subject invention can be used to conduct an escape test and a well-matched, paired motor control test, inclusively, within the same apparatus, and because the painful condition and the aversive, non-painful condition can be rapidly produced and removed within each chamber, the apparatus 10 of the subject invention can be used to evaluate the pain sensitivity of a test animal within the same day and even within the same hour. This is important because the physiological and behavioral status of many test animals can vary within a month or even within a day, affecting experimental results.

The means for automation can include one or more computer programs that can control the activation, deactivation, and intensity of the means for producing the painful condition (e.g., set the floor temperatures) and the means for producing the aversive, non-painful condition (e.g., light sources), as well as sense and record the movements of the test animal 30 within the apparatus 10, e.g., between the two chambers 12, 14. For example, the pain sensitivity test can be conducted on a test animal and the results can be compared with that of the test of general motivation and motor ability as a control. Both tests and the comparison of results can be conducted through automation. The means for automating one or more of the means for producing a painful condition the first and second chambers, the means for producing an aversive, non-painful condition in the first and second chambers, and the means for sensing the presence of the test animal within the first and second chambers can be in operable communication with an interface device to receive commands from an operator of the device. The interface device can display menus for directing the automation means, e.g., specifying various experiment parameters and conditions within the first and second chambers.

The chamber walls can be constructed of a variety of materials, such as plastic, wood, metal, or glass. The chamber walls can be completely or partially transparent, or opaque. Preferably, the chamber walls are transparent (e.g., constructed of PLEXIGLAS), permitting easy observation of the test animal within the apparatus 10. In this case, it is also preferable to create a one-way mirror effect by tinting the walls of the chambers and dimming the light in the outside environment to minimize distractions for the test animal. The chambers can be a variety of shapes, with the number of walls depending upon the shape.

Preferably, the chambers 12, 14 have lids or are otherwise covered to minimize outside stimuli, e.g., from the laboratory environment.

In a specific embodiment, the first and second chambers 12, 14 are adjacent to one another, each chamber having three walls and a fourth wall 60, which is shared between the two chambers 12, 14. In this embodiment, the fourth wall 60 roughly bisects the apparatus 10, but incompletely separates the two chambers 12, 14, and defines the passageway 16 that connects the chambers 12, 14, as shown in FIG. 1.

The apparatus of the subject invention preferably includes two chambers, but may include more chambers and more passageways connecting the chambers, as required by the specific experiment protocols.

If one or more light sources that radiate excessive amounts of heat are used as the means for producing a painful condition in either chamber, it is preferable to block the heat with a heat-absorbing filter. If means for independently heating and cooling the floors of each chamber 12, 14 are used as the means for producing a painful condition, an excessive rise of the ambient temperature within the chambers 12, 14 can be prevented by forced air circulation, as with a fan in one or more chambers.

Preferably, the test animal 30 is not restrained in the apparatus 10, thereby eliminating the confounding factor of restraint stress, which is known to affect pain sensitivity.

A treatment being tested with the apparatus 10 of the subject invention can include administration of a substance (e.g., a drug or nutraceutical), a surgical procedure, or other intervention that is being evaluated for its effects on pain sensitivity or general effects on operant behavior. A treatment being tested can be either hyper-analgesic (decreasing normal pain sensitivity) or hypo-analgesic (increasing pain sensitivity beyond that which is normal). Furthermore, the treatment can be genetic manipulation conducted on either the test animal itself, or one or more of the test animal's forebears. For example, "knock out" animals can be tested with the apparatus of the subject invention to study the effects of the knocked out gene or genes on nociception with or without further treatment. The test animal 30 can be suffering from a disease state or other pathological condition. The pain sensitivity of the test animal 30 suffering from a disease state or pathological condition can be evaluated with the subject apparatus 10, with or without treatment. Therefore, the apparatus of the subject invention can be used to test the general pain sensitivity exhibited by a test animal 30, in whatever condition the test animal 30 is in, naturally occurring or artificially induced.

As used herein, the terms "operable communication" and "operably connected" mean that the particular elements are connected in such a way that they cooperate to achieve their intended function or functions. The "connection" may be direct or indirect, physical or remote.

As used herein, references to "first," "second," and the like (e.g., first and second chambers, first and second light sources) are intended to identify a particular feature of which there are at least two. However, these references are not intended to confer any order in time, structural orientation, or sidedness (e.g., left or right) with respect to the particular feature.

As used herein, it should be understood that the term "painful condition" is a relative term, meaning that the condition will be potentially painful, but the actual pain perceived by the test animal 30 will ultimately depend upon the pain sensitivity of the test animal 30.

All patents and publications referred to or cited herein are incorporated by reference in their entirety to the extent they are not inconsistent with the explicit teachings of this specification.

Following is an example which illustrates procedures for practicing the invention. The example should not be construed as limiting.

EXAMPLE 1

Operant Test Apparatus Utilizing Light and Thermoelectric Modules

The first and second chambers 12, 14 are adjacent to one another, each chamber having three walls and a fourth wall 60, which is shared between the two chambers 12, 14. The fourth wall 60 roughly bisects the apparatus 10, but incompletely separates the two chambers 12, 14, and defines the passageway 16 that connects the chambers 12, 14, as shown in FIG. 1. The first chamber 12 has two side walls 60, 62 and one end wall 64. The second chamber 14 has two side walls 66, 68, and one end wall 70. The first chamber 12 has two light sources 40 and 42, one within the side wall 62 most distant from the passageway 16 and the other in the end wall 64. The second chamber 14 has two light sources 44, 46, one within the side wall 68 most distant from the passageway 16, and one within the end wall 70, as shown in FIG. 1. The chamber walls containing light sources are sufficiently transparent to allow passage of light into the respective chambers at aversive levels.

Figure 2A:
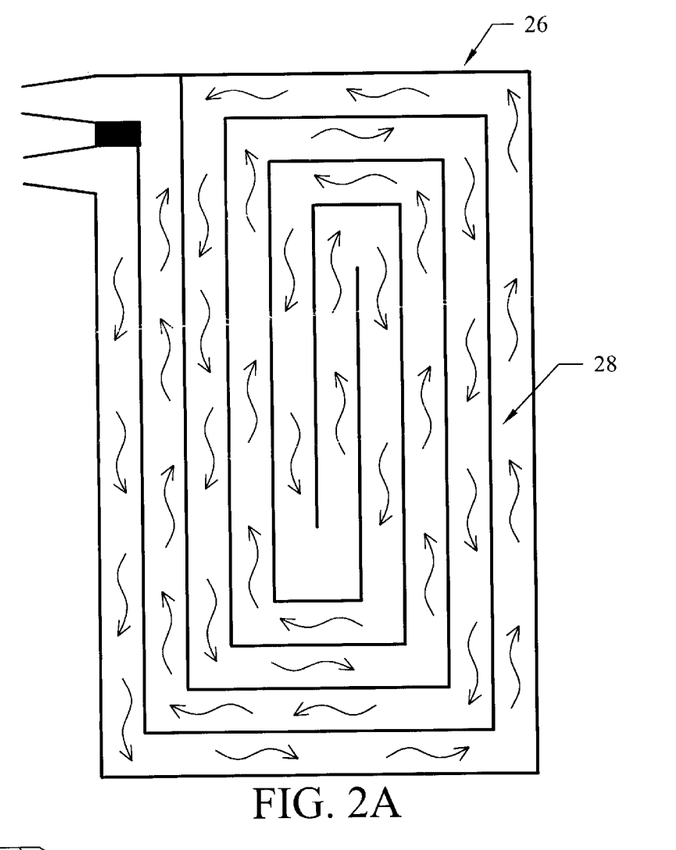
FIG. 2A shows a transparent overhead view of the floor of a chamber in one embodiment of the subject invention. Channels for flow of heated or cooled fluid through the heat sink are shown.
Figure 2B:
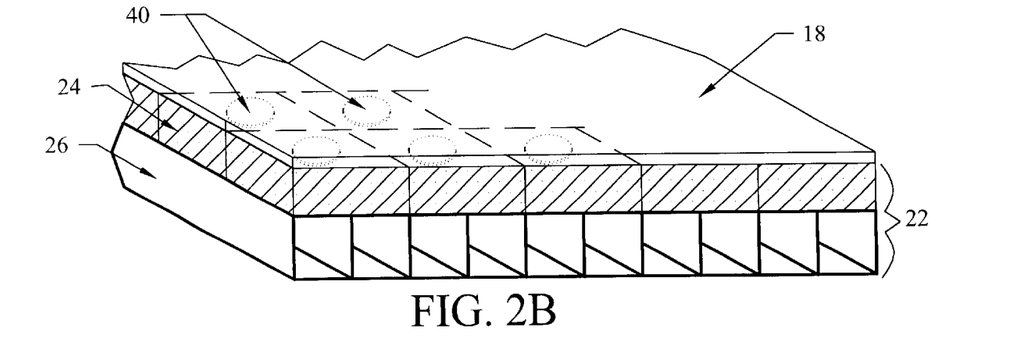
FIG. 2B shows a side view of the floor of a chamber in one embodiment of the subject invention. The floor, thermistors, thermoelectric-modules, and heat sink are shown.

The chamber floors 12, 14 are composed of copper and the means for heating and cooling 22 the floors are one or more thermoelectric modules (TEMs) 24 and a heat sink 26, with the TEMs between the chamber floors and the heat sink, as shown in FIG. 2B. The heat sink 26 is a fluid-type heat sink composed of aluminum and containing channels 28 for fluid circulation adjacent to the TEMs 24, as shown in FIG. 2A. Fluid can be continuously pumped through the heat sink 26 at 15 liters/minute, serving as a thermal carrier. Preferably, the fluid is a mixture of ethylene glycol (about 20%) and distilled water (about 80%). The temperature of the chamber floors 18, 20 can be adjusted from freezing temperatures, through the tolerable range of heat, to painfully hot temperatures, as required by the specific experimental situation.

TEMs 24, also known as Peltier devices, are commercially available (MELCOR, Trenton, N.J.) and used to move heat (i.e., a heat pump). When current from a power source passes through the junction of two different types of conductors, it results in a temperature change. The current causes heat to move from one side of the TEM to the other, creating a hot side and a cold side on the TEM. At the cold junction, energy (heat) is absorbed by electrons as they pass from a low energy level in the p-type semiconductor element, to a higher energy level in the n-type semiconductor element. The power supply provides the energy to move the electrons through the system. At the hot junction, energy is expelled to a heat sink as electrons move from a high energy level element (n-type) to a lower energy level element (p-type).

Thermoelectric cooling "couples" can be made from two elements of semiconductor, such as bismuth telluride, doped to create either an excess (n-type) or deficiency (p-type) of electrons. Heat absorbed at the cold junction is pumped to the hot junction at a rate proportional to current passing through the circuit and the number of couples. Thermoelectric cooling couples are combined and arrayed in a module, where they are connected electrically in series and thermally in parallel (i.e., pumping together in the same direction). Modules are available in a variety of sizes, shapes, operating currents, operating voltages, and ranges of heat pumping capacity.

A plurality of TEMs 24 can be used side-by-side to increase the amount of heat pumped, as shown in FIG. 2B, or they can be stacked on top of one another (i.e., "cascades" or "multistage TEMs") to increase the temperature difference across the TEM 24. Typically, when the temperature difference doesn't need to be more than about 60° C. to about 67° C., single-stage TEMs are sufficient. If the temperature difference needs to be greater than about 60° C. to about 67° C., cascades should be considered. The amount of heat pumped through the TEM 24 is directly proportional to the power supplied.

Preferably, the channels 28 of the heat sink 26 are arranged such that the temperature is uniform (e.g., within about ±0.1° C.) across the entire surface of the heat sink. The fluid circulation is closed and the system includes a 7-liter bath containing the water/ethylene glycol medium and a pump of about 15 liters/minute capacity. A temperature controller, such as a DPDT relay, which is wired in the classic polarity-reversal configuration, can be used to switch between heating and cooling modes. One or more thermistor probes 40 (thermally sensitive resistor), shown in phantom in FIG. 2B, can be used to sense the temperature of each of the chamber floors. The thermister probes 40 can be located between each TEM 24 and the chamber floor. In order to maintain close contact between the chamber floors 12, 14 and the TEMs 24, the underside of the chamber floors 12, 14 can have recesses for containing the thermistor probes 40. In FIG. 2B, the phantom lines surrounding the thermistor probes 40 represent the individual TEMs 24 beneath the chamber floor.

The temperature controller, which is in operable communication with the thermistor probe 40 and each TEM 24, can be used to set the temperature and provide the DC current that drives the TEMs 24. The use of electronically regulated TEMs 40 compensates for thermal disturbances such as paw contact or urine released by the test animal 30. Furthermore, this design allows temperatures of the chamber floors 18, 20 to be changed within seconds, e.g., to reverse the temperature between chambers 12, 14, in order to prevent the test animal 30 from associating one of the chambers with a certain experimental condition.

What is claimed is:

1. An apparatus for testing pain sensitivity in a test animal, comprising:
   a first chamber;
   means for producing a painful condition within said first chamber, wherein said means for producing a painful condition within said first chamber can rapidly produce and rapidly remove a painful condition within said first chamber;
   means for producing an aversive, non-painful condition within said first chamber, wherein said means for producing an aversive, non-painful condition within said first chamber can rapidly produce and rapidly remove an aversive, non-painful condition within said first chamber;
   a second chamber, wherein said second chamber is connected to said first chamber by a passageway of sufficient size to permit the test animal to pass between said first and second chambers; and wherein said means for producing a painful condition in said first chamber and said means for producing an aversive, non-painful condition in said first chamber can each motivate the test animal to move from said first chamber through said passageway to said second chamber;
   means for producing a painful condition within said second chamber, wherein said means for producing a painful condition in said second chamber can rapidly produce and rapidly remove a painful condition within said second chamber; and
   means for producing an aversive, non-painful condition within said second chamber, wherein said means for producing an aversive, non-painful condition within said second chamber can rapidly produce and rapidly remove an aversive, non-painful condition within said second chamber, and wherein said means for producing a painful condition in said second chamber and said means for producing an aversive, non-painful condition within said second chamber can each motivate the test animal to move from said second chamber to said first chamber through said passageway.

2. The apparatus, according to claim 1, wherein a painful condition can be produced in each of said first and second chambers in about 30 seconds or less, wherein an aversive, non-painful condition can be produced in each of said first and second chambers in about 30 seconds or less, wherein a painful condition can be removed from each of said first and second chambers in about 30 seconds or less, and wherein an aversive, non-painful condition can be removed from each of said first and second chambers in about 30 seconds or less.

3. The apparatus, according to claim 1, wherein a painful condition can be produced in each of said first and second chambers in about 10 seconds or less, wherein an aversive, non-painful condition can be produced in each of said first and second chambers in about 10 seconds or less, wherein a painful condition can be removed from each of said first and second chambers in about 10 seconds or less, and wherein an aversive, non-painful condition can be removed from each of said first and second chambers in about 10 seconds or less.

4. The apparatus, according to claim 1, wherein a painful condition can be produced in each of said first and second chambers in about 5 seconds or less, wherein an aversive, non-painful condition can be produced in each of said first and second chambers in about 5 seconds or less, wherein a painful condition can be removed from each of said first and second chambers in about 5 seconds or less, and wherein an aversive, non-painful condition can be removed from each of said first and second chambers in about 5 seconds or less.

5. The apparatus, according to claim 1, wherein said first and second chambers each have a floor for supporting the test animal, wherein said first and second chamber floors are composed of a thermally conductive material, wherein said means for producing a painful condition in said first chamber comprises a means for independently heating and cooling said first chamber floor to temperatures that are painful to the test animal, and wherein said means for producing a painful condition in said second chamber comprises a means for independently heating and cooling said second chamber floor to temperatures that are painful to the test animal.

6. The apparatus, according to claim 5, wherein said means for independently heating and cooling said first and second chamber floors are capable of independently modulating the temperature of said first and second chamber floors, respectively, about 10° C. in about ten seconds or less, within a temperature range of about 0° C. to about 60° C.

7. The apparatus, according to claim 5, wherein said means for independently heating and cooling said first and second chamber floors are capable of independently modulating the temperature of said first and second chamber floors, respectively, about 10° C. in about five seconds or less, within a temperature range of about 0° C. to about 60° C.

8. The apparatus, according to claim 5, wherein said means for independently heating and cooling said first chamber floor comprises one or more thermoelectric modules located beneath said first chamber floor, and wherein said means for independently heating and cooling said second chamber floor comprises one or more thermoelectric modules located beneath said second chamber floor.

9. The apparatus, according to claim 8, wherein means for independently heating and cooling said first chamber floor further comprises a heat sink located beneath said one or more thermoelectric modules beneath said first chamber floor, and wherein said means for independently heating and cooling said second chamber floor further comprises a heat sink located beneath said one or more thermoelectric modules beneath said second chamber floor.

10. The apparatus, according to claim 9, wherein said thermally conductive material is copper and wherein said heat sinks are aluminum fluid-type heat sinks containing channels for fluid circulation.

11. The apparatus, according to claim 5, wherein said means for independently heating and cooling said first and second chambers are in operable communication with a temperature control device.

12. The apparatus, according to claim 1, wherein said means for producing an aversive, non-painful condition in said first chamber comprises one or more light sources for lighting said first chamber, and wherein said means for producing an aversive, non-painful condition in said second chamber comprises one or more light sources for lighting said second chamber.

13. The apparatus, according to claim 12, wherein said first chamber has one or more walls, wherein said second chamber has one- or more walls, wherein said one or more light sources for lighting said first chamber are located on or within one or more walls of said first chamber, and wherein said one or more light sources for lighting said second chamber are located on or within one or more walls of said second chamber.

14. The apparatus, according to claim 1, further comprising means for sensing the passage of the animal through said passageway.

15. The apparatus, according to claim 14, wherein said sensing means comprises one or more infrared beam emitters and detectors operably positioned at said passageway, wherein said one or more infrared beam emitters and detectors produce one or more infrared beams, and wherein interruption of said one or more infrared beams by the test animal produces a signal indicating that the test animal has passed through said passageway.

16. The apparatus, according to claim 1, further comprising means for sensing the presence of the test animal within said first chamber and means for sensing the presence of the test animal within said second chamber.

17. The apparatus, according to claim 16, wherein said means for sensing the presence of the test animal within said first chamber comprises one or more infrared beam emitters and detectors operably positioned within said first chamber, wherein said means for sensing the presence of the test animal within said second chamber comprises one or more infrared beam emitters and detectors operably positioned within said second chamber, thereby producing one or more infrared beams within each of said first and second chambers, wherein interruption of said one or more infrared beams in said first chamber produces a signal indicating the presence of the test animal within said first chamber, and wherein interruption of said one or more infrared beams in said second chamber produces a signal indicating the presence of the test animal within said second chamber.

18. The apparatus, according to claim 16, wherein said apparatus further comprises means for measuring the amount of time the test animal is present in said first chamber and said second chamber.

19. The apparatus, according to claim 16, wherein said apparatus further comprises means for automating said means for producing an aversive, non-painful condition in said first chamber in response to said means for sensing the presence of the test animal within said first chamber, and means for automating said means for producing an aversive, non-painful condition in said second chamber in response to said means for sensing the presence of the test animal within said second chamber, wherein when the test animal passes through said passageway from said first chamber to said second chamber, said means for producing an aversive, non-painful condition in said second chamber is automatically activated or automatically deactivated, and wherein when the test animal passes through said passageway from said second chamber to said first chamber, the means for producing an aversive, non-painful condition in said first chamber is automatically activated or automatically deactivated.

20. The apparatus, according to claim 16, wherein said apparatus further comprises means for automating said means for a painful condition in said first chamber in response to said means for sensing the presence of the test animal within said first chamber, and means for automating said means for producing a painful condition in said second chamber in response to said means for sensing the presence of the test animal within said second chamber, wherein when the test animal passes through said passageway from said first chamber to said second chamber, said means for producing a painful condition in said second chamber is automatically activated or automatically deactivated, and wherein when the test animal passes through said passageway from said second chamber to said first chamber, the means for producing a painful condition in said first chamber is automatically activated or automatically deactivated.

21. The apparatus, according to claim 1, wherein the shape and dimensions of said first chamber and said second chamber are substantially identical.

22. A method for testing the pain sensitivity of a test animal, comprising the steps of:

introducing the test animal into the apparatus of claim 1;

activating said means for producing an aversive, non-painful condition in said first chamber;

activating said means for producing a painful condition in said second chamber when said second chamber is occupied by the test animal, thereby motivating the test animal to move through said passageway to said first chamber if the test animal perceives pain;

measuring the escape latency exhibited by the test animal.

23. The method, according to claim 22, wherein said escape latency is the amount of time the test animal spends in said second chamber after said means for producing a painful condition is activated in said second chamber.

24. The method, according to claim 22, further comprising comparing said escape latency with a control escape latency.

25. The method, according to claim 24, wherein said control escape latency is exhibited by the test animal when the test animal is introduced in the apparatus of claim 1, said means for producing a painful condition in said first chamber is not activated, said means for producing a painful condition in said second chamber is not activated, said means for producing an aversive, non-painful condition in said first chamber is activated if said first chamber is occupied by the test animal, thereby motivating the test animal to move through said passageway to said second chamber, and said means for producing an aversive, non-painful condition in said second chamber is activated if said second chamber is occupied by the test animal, thereby causing the test animal to move through said passageway to said first chamber.

26. The method, according to claim 24, wherein pain sensitivity in the test animal can be inferred if the escape latency is lower than that of the control escape latency.

27. The method, according to claim 22, wherein said first and second chambers each have a floor for supporting the test animal, wherein said first and second chamber floors are each composed of a thermally conductive material, wherein said means for producing a painful condition in said first chamber comprises a means for independently heating and cooling said first chamber floor to temperatures that are painful to the test animal, and wherein said means for producing a painful condition in said second chamber comprises means for independently heating and cooling said second chamber floor to temperatures that are painful to the test animal.

28. The method, according to claim 27, wherein said means for independently heating and cooling said first chamber floor comprises one or more thermoelectric modules located beneath said first chamber floor, and wherein said means for independently heating and cooling said second chamber floor comprises one or more thermoelectric modules located beneath said second chamber floor.

29. The method, according to claim 28, wherein said means for independently heating and cooling said first chamber floor further comprises a heat sink located beneath said one or more thermoelectric modules beneath said first chamber floor, and wherein said means for independently heating and cooling said second chamber floor further comprises a heat sink located beneath said one or more thermoelectric modules beneath said second chamber floor.

30. The method, according to claim 22, wherein said apparatus further comprises means for sensing the presence of the test animal within said first chamber and means for sensing the presence of the test animal within said second chamber.

31. The method, according to claim 30, wherein said means for sensing the presence of the test animal within said first chamber comprises one or more infrared beam emitters and detectors operably positioned within said first chamber, wherein said means for sensing the presence of the test animal within; said second chamber comprises one or more infrared beam emitters and detectors operably positioned within said second chamber, thereby producing one or more infrared beams within each of said first and second chambers, wherein interruption of said one or more infrared beams in said first chamber produces a signal indicating the presence of the test animal within said first chamber, and wherein interruption of said one or more infrared beams in said second chamber produces a signal indicating the presence of the test animal within said second chamber.

32. A method for determining pain sensitivity in a test animal, comprising the steps of:

introducing the test animal into the apparatus of claim 1;

activating said means for producing an aversive, non-painful condition in said first chamber;

activating said means for producing a painful condition in said second chamber when said second chamber is occupied by the test animal, thereby motivating the test animal to move through said passageway to said first chamber;

deactivating said means for producing an aversive, non-painful condition in said first chamber;

deactivating said means for producing a painful condition in said second chamber;

activating said means for producing an aversive, non-painful condition in either said first chamber or said second chamber;

activating said means for producing a painful condition in whichever of said first and second chambers is occupied by the test animal, thereby motivating the test animal to move through said passageway to the opposite chamber; and measuring the place preference exhibited by the test animal.

33. The method, according to claim 32, wherein the place preference is the environment the test animal spends more time in, wherein the environment is selected from the group consisting of:

said first chamber, when said means for producing an aversive, non-painful condition is activated in said first chamber; said second chamber, when said means for producing an aversive, non-painful condition is activated in said second chamber; or both said first chamber and said second chamber, when both said means for producing an aversive, non-painful condition in said first chamber and said second chamber are activated; and said first chamber, when said means for producing a painful condition is activated in said first chamber; said second chamber, when said means for producing a painful condition is activated in said second chamber; or both said first chamber and said second chamber, when both said means for producing painful condition in said first chamber and said second chamber are activated, respectively.

34. The method, according to claim 32, wherein pain sensitivity is inferred if the test animal spends more time in:
   said first chamber, when said means for producing a painful condition in said first chamber is deactivated and said means for producing an aversive non-painful condition in said first chamber is activated;
   said second chamber, when said means for producing a painful condition in said second chamber is deactivated and said means for producing an aversive, non-painful condition in said second chamber is activated; or
   both said first chamber and said second chamber, when both said means for producing a painful condition in said first chamber and said second chamber are deactivated and both said means for producing an aversive, non-painful condition in said first chambers and said second chamber are activated, respectively.

35. The method, according to claim 32, wherein said first and second chambers each have a floor for supporting the test animal, wherein said first and second chamber floors are each composed of a thermally conductive material, wherein said means for producing a painful condition in said first chamber comprises a means for independently heating and cooling said first chamber floor to temperatures that are painful to the test animal, and wherein said means for producing a painful condition in said second chamber comprises means for independently heating and cooling said second chamber floor to temperatures that are painful to the test animal.

36. The method, according to claim 35, wherein said means for independently heating and cooling said first chamber floor comprises one or more thermoelectric modules located beneath said first chamber floor, and wherein said means for independently heating and cooling said second chamber floor comprises one or more thermoelectric modules located beneath said second chamber floor.

37. The method, according to claim 36, wherein said means for independently heating and cooling said first chamber floor further comprises a heat sink located beneath said one or more thermoelectric modules beneath said first chamber floor, and wherein said means for independently heating and cooling said second chamber floor further comprises a heat sink located beneath said one or more thermoelectric modules beneath said second chamber floor.

38. The method, according to claim 32, wherein said apparatus further comprises means for sensing the presence of the test animal within said first chamber and means for sensing the presence of the test animal within said second chamber.

39. The method, according to claim 38, wherein said means for sensing the presence of the test animal within said first chamber comprises one or more infrared beam emitters and detectors operably positioned within said first chamber, wherein said means for sensing the presence of the test animal within said second chamber comprises one or more infrared beam emitters and detectors operably positioned within said second chamber, thereby producing one or more infrared beams within each of said first and second chambers, wherein interruption of said one or more infrared beams in said first chamber produces a signal indicating the presence of the test animal within said first chamber, and wherein interruption of said one or more infrared beams in said second chamber produces a signal indicating the presence of the test animal within said second chamber.

* * * * *

UNITED STATES PATENT AND TRADEMARK OFFICE
CERTIFICATE OF CORRECTION

PATENT NO. : 6,644,244 B2
DATED : November 11, 2003
INVENTOR(S) : Andre Paul Mauderli and Charles J. Vierck It is certified that error appears in the above-identified patent and that said Letters Patent is hereby corrected as shown below:

Column 1,
Line 27, "*Neuronmethods, Psychopharmachology*" should read -- *Neuromethods, Psychopharmachology* --
Line 43, "society [1983] pp. 117-132" should read -- society [1983a] pp. 117-132 --

Column 4,
Line 3, "and a specific compartment or location.
         . In addition,"
should read -- and a specific compartment or location. In addition, --

Column 7,
Line 43, "chamber floor, each heat:sink" should read -- chamber floor, each heat sink --

Signed and Sealed this

Twenty-ninth Day of June, 2004

JON W. DUDAS
*Acting Director of the United States Patent and Trademark Office*